United States Patent [19]

Harris

[11] Patent Number: 4,723,037

[45] Date of Patent: Feb. 2, 1988

[54] PROCESS FOR MAKING 1,3-DIOXANE DERIVATIVES

[75] Inventor: Gregory D. Harris, Macclesfield, United Kingdom

[73] Assignee: Imperial Chemical Industries PLC, London, England

[21] Appl. No.: 670,016

[22] Filed: Nov. 9, 1984

[30] Foreign Application Priority Data

Nov. 11, 1983 [GB] United Kingdom ................. 8330120

[51] Int. Cl.$^4$ ..................... C07C 59/48; C07C 143/72
[52] U.S. Cl. ..................................... 562/470; 564/99; 549/373; 549/375
[58] Field of Search ....................... 562/470, 455, 434; 564/99; 560/60

[56] References Cited

U.S. PATENT DOCUMENTS 4,567,197  1/1986  Brewster .......................... 549/373

FOREIGN PATENT DOCUMENTS 0094239  11/1983  European Pat. Off. ............ 549/369
0076684   6/1983  Portugal ............................. 549/369

OTHER PUBLICATIONS

Bull. Soc. Chim. Japan, 1968, 41, 1468–1471, Takeda et al.
Impadoc Search Report of EP 94239–1/86.

*Primary Examiner*—Glennon H. Hollrah
*Assistant Examiner*—D. L. Dinner
*Attorney, Agent, or Firm*—Cushman, Darby & Cushman

[57] ABSTRACT

The invention provides a novel process for making novel (4-phenyl-1,3,-dioxan-cis-5-yl)alkenoic acids of the formula I in which Ra and Rb are independently hydrogen, alkenyl, alkyl, halogenoalkyl, pentafluorophenyl, aryl or aryl-(1–4C)alkyl; or Ra and Rb together are polymethylene; Rc is hydroxy or (1–6C)alkanesulphonamido, A is vinylene, n is 1, Y is polymethylene, and benzene ring B bears various optional substituents. The process involves the reaction of an aldehyde of formula II with an ylid to give an erythro-diol of formula III which is then cyclized to the required dioxane derivative of formula I. The invention also provides a novel process for making the aldehydes of formula II from the corresponding lactols of formula IIa, which are themselves obtained with the correct trans-stereochemistry by two selective reductions of a trans-phenyl-paraconic acid of formula V. The compounds of formula I are useful as therapeutic agents.

2 Claims, No Drawings

PROCESS FOR MAKING 1,3-DIOXANE DERIVATIVES

This invention concerns a novel chemical process for the production of novel (4-phenyl-1,3-dioxan-cis-5-yl)alkenoic acid derivatives which antagonise one or more of the actions of thromboxane $A_2$ ($TXA_2$) and are of value as therapeutic agents. The invention is also concerned with various 2-phenyl-tetrahydrofuran derivatives which are valuable chemical intermediates, for example for use in the above mentioned process.

In European patent application, publication No. 94239A2, (hereafter EPA No. 94239), there is described a series of (4-phenyl-1,3-dioxan-cis-5-yl)alkenoic acids of the formula I (set out hereinafter) where Ra and Rb are independently hydrogen, (2–6C)alkenyl, (1–8C)alkyl optionally bearing up to three halogeno substituents, pentafluorophenyl, aryl or aryl-(1–4C)alkyl, the latter two of which may optionally bear up to three substituents selected from halogeno, (1–6C)alkyl, (1–6C)alkoxy, (1–4C)alkenylenedioxy, trifluoromethyl, cyano, nitro, hydroxy, (2–6C)alkanoyloxy, (1–6C)alkylthio, (1–6C)alkanesulphonyl, (1–6C)alkanoylamino, and oxapolymethylene of 2 to 4 carbon atoms, provided that when both Ra and Rb are alkyl or alkenyl, the total number of carbon atoms in Ra and Rb taken together is 8 or less; or Ra and Rb together form polymethylene of 2 to 7 carbon atoms, optionally bearing one or two (1–4C)alkyl substituents; Rc is hydroxy, (1–6C)alkoxy or (1–6C)alkanesulphonoamido; n is the integer 1 or 2; A is ethylene or vinylene; Y is polymethylene of 2 to 5 carbon atoms optionally bearing (1–4C)alkyl as a substituent; benzene ring B optionally bears one or two substituents selected from halogeno, (1–6C)alkyl, (1–6C)alkoxy, hydroxy, (1–6C)alkanoyloxy, (1–6C)alkanoylamino, trifluoromethyl and nitro; and the substituents at positions 4 and 5 of the dioxane ring have cis-relative stereochemistry; or for those compounds wherein Rc is hydroxy, a salt thereof with a base affording a physiologically acceptable cation. The compounds are disclosed as antagonising one or more of the actions of thromboxane $A_2$ and are of value as therapeutic agents.

The compounds of formula I contain at least two asymmetric carbon atoms (i.e. at $C_4$ and $C_5$ of the dioxane ring) and may exist and be isolated in racemic and optically active forms. In addition those compounds of formula I wherein A is vinylene exist, and may be isolated, in separate stereoisomeric forms ('E' and 'Z') about that group. The terms Ra, Rb and Rc etc, are used to depict generic radicals and have no other significance.

Specific combinations of Ra and Rb which are disclosed as preferred are, by way of example,:

(i) Ra and Rb are both hydrogen, methyl, ethyl, propyl, butyl or trifluoromethyl;

(ii) one of Ra is hydrogen and the other is trifluoromethyl, chloromethyl, benzyl, isopropyl, hexyl, octyl, phenyl (optionally bearing 1 or 2 fluoro, chloro, bromo, methyl, methoxy, trifluoromethyl, hydroxy, cyano, methylthio or acetamido), phenyl bearing methylenedioxy or methyleneoxymethylene ($-CH_2OCH_2-$), pentafluorophenyl, 1-naphthyl or 2-naphthyl; and (iii) Ra and Rb together form trimethylene, tetramethylene, pentamethylene, hexamethylene or a group of the formula: $-CH_2CH_2.CHCH_3.CH_2CH_2-$.

Specific preferred values for Ra or Rb when it is a mono or disubstituted phenyl are, for example, 2-fluoro-, 3-fluoro-, 4-fluoro-, 2-chloro-, 3-chloro-, 4-chloro-, 2-bromo-, 3-bromo-, 4-bromo-, 2-methyl-, 3-methyl-, 4-methyl-, 2-methoxy-, 3-methoxy-, 4-methoxy-, 2-trifluoromethyl-, 3-trifluoromethyl, 4-trifluoromethyl-, 3-hydroxy-, 4-cyano-, 4-methylthio-, 4-acetamido-, 3,4-dichloro-, 2,4-dimethyl-, 3,4-methylenedioxy- and 3,4-(methyleneoxymethylene)-phenyl.

Specific preferred values for benzene ring B are, for example, when it is phenyl, or 2-fluoro-, 2-chloro-, 2-bromo-, 2-methyl-, 2-ethyl-, 2-isopropyl-, 2-methoxy-, 2-hydroxy-, 3-fluoro- or 3-chloro-phenyl.

A further preferred group of acids desclosed in EPA94239 comprises compounds of the formula Ib wherein:

(i) Ra and Rb are both hydrogen, methyl, ethyl, propyl, butyl, or trifluoromethyl;

(ii) or together form trimethylene, tetramethylene, pentamethylene, hexamethylene or a group of the formula: $-CH_2CH_2.CHCH_3.CH_2CH_2-$; or (iii) Ra is (3–8C)alkyl, trifluoromethyl, chloromethyl, 2-chloroethyl, pentafluorophenyl, or phenyl, benzyl or naphthyl, the last three of which may optionally bear 1 or 2 halogeno, (1–4C)alkyl, (1–4C)alkoxy, trifluoromethyl, hydroxy, cyano, (1–4C)alkylthio or (1–4C)alkanoylamino substituents, or a methylenedioxy or methyleneoxymethylene substituent, and Rb is hydrogen;

benzene ring B is unsubstituted or is 2-halogeno-, 2-(1–4C)alkyl-, 2-(1–4C)alkoxy-, 2-hydroxy- or 3-halogeno-phenyl;

Ra and the substituents at the 4- and 5-positions of the dioxane ring have cis-relative stereochemistry; and the carbon atoms adjacent to the vinylene group have the indicated cis-relative stereochemistry; or a salt thereof with a base affording a physiologically acceptable cation; or a methyl or ethyl ester thereof; or a methanesulphonamido, ethanesulphonamido or 1-methylethanesulphonamido.

Particular salts of compounds of formula Ib or I (wherein Rc is hydroxy) which are disclosed include, for example, alkali metal and alkaline earth metal salts such as lithium, sodium, potassium, magnesium and calcium salts, aluminium and ammonium salts, and salts with organic amines or quaternary bases forming physiologically acceptable cations.

A preferred compound disclosed in EPA No. 94239 is 5(Z)-7-(2,2-dimethyl-4-o-methoxyphenyl-1,3-dioxan-cis-5-yl)heptenoic acid.

A major problem in the production of compounds of the formula I lies in arranging for the correct cis-relative stereochemistry at positions 4,5 of the dioxane ring. In EPA No. 94239, this problem is solved by chromatographic separation of cis-/trans-stereoisomeric mixtures at one or more stages in the synthetic sequence. The process of the present invention avoids such a separation of stereoisomers by incorporating the correct relative stereochemistry at an early point in the synthetic procedure. The process of the invention also avoids the use of ozone which is used in the synthetic sequence disclosed in EPA No. 94239 and is readily adapted to produce optically active forms of the formula I compounds.

According to the invention there is provided a process for the manufacture of a compound of formula I as defined hereinbefore but wherein n is 1, A is vinylene and Rc is hydroxy or (1–6C)alkanesulphonamido which comprises the steps of:

(i) reacting an erythro-4-hydroxy-3-hydroxymethyl-4-phenylbutyraldehyde of the formula II, or an alkali metal salt thereof, with an ylid of the formula:

wherein Rd is (1-6C)alkyl (especially methyl or ethyl) or aryl (especially phenyl) and when Rc is hydroxy, Q stands for —OM in which M is an alkali metal such as lithium, sodium or potassium and, when Rc is (1-6C)alkanesulphonamido, Q stands for —NM.SO$_2$Re in which Re is (1-6C)alkyl such as methyl or ethyl and M has the meanings stated above, to give after acidification an erythro-diol of the formula III wherein Rf has the limited meaning for Rc defined above; and (ii) reacting the diol of formula II, or a mono (1-6C)alkanesulphonyl or arenesulphonyl ester thereof, with a carbonyl compound of the formula RaRb.CO, or an acetal hemiacetal or hydrate thereof.

It will be appreciated that the above process can be readily adapted to the production of compounds of the formula I wherein A is ethylene by interposing a conventional catalytic hydrogenation step after the above Wittig reaction (i) or cyclisation reaction (ii). Such a hydrogenation may be carried out in a suitable solvent or diluent, for example a (1-4C)alkanol (such as ethanol or 2-propanol), optionally in the presence of water, and at a temperature in the range, for example, 15° to 35° C., using hydrogen at a pressure of, for example, 1 to 2 atmospheres. A suitable catalyst is, for example, a noble metal catalyst such as palladium metal conveniently on an inert support as carbon, barium sulphate or barium carbonate.

Similarly, when a compound of formula I wherein Rc is (1-6C)alkoxy is required, the corresponding acid of formula I wherein Rc is hydroxy, or a reactive derivative thereof, is esterified using a conventional procedure, starting from the free acid or a reactive derivative.

When a free acid of formula I is used, it is particularly convenient to perform the process in the presence of a suitable dehydrating agent, for example dicyclohexylcarbodiimide, in the presence of a suitable solvent or diluent for example tetrahydrofuran, acetone, methylene chloride or 1,2-dimethoxyethane, at a temperature in the range, for example, 10° to 50° C., but preferably at or near room temperature.

A suitable reactive derivative of an acid of formula I is, for example, an acid chloride, bromide, anhydride, mixed anhydride with formic acid, or an azide, which may be produced from the free acid in conventional manner. When such a derivative is used, no additional dehydrating agent is necessary, and the (1-6C)alkanol is conveniently present in large excess, optionally diluted with a suitable diluent or solvent such as an ether, for example tetrahydrofuran or 1,2-dimethoxyethane.

Compounds of formula I wherein Rc is (1-6C)alkanesulphonamido may be obtained by carrying out the above process to produce an acid of formula I wherein Rc is hydroxy followed by a conventional sulphonamidation analogous to the above described esterification. Thus, for example a free acid of formula I wherein Rc is hydroxy may be reacted with a (1-6C)alkanesulphonamide together with a suitable dehydrating agent, for example dicyclohexylcarbodiimide, optionally together with an organic base, for example 4-dimethylaminopyridine, in the presence of a suitable solvent or diluent, for example methylene chloride at a temperature in the range, 10° to 50° C., but preferably at or near room temperature. Alternatively, a reactive derivative of an acid of formula I, wherein Rc is hydroxy, for example an acid halide (such as the acid chloride) may be reacted with an alkali metal salt (such as the sodium salt) of the appropriate (1-6C)alkanesulphonamide, conveniently at or near room temperature and in a suitable solvent or diluent, for example an ether, N,N-dimethylformamide or methylene chloride.

When a salt of a compound of formula I wherein Rc is hydroxy is required, it may be obtained, for example, by reaction with the appropriate base affording a physiologically acceptable cation.

Further, when an optically active form of a compound of formula I is required, the process of the invention is carried out using an optically active starting material of formula II or III. Alternatively, when Rc is hydroxy, a racemic form of the said compound may be reacted with an optically active form of a suitable organic base, for example ephedrine, N,N,N-trimethyl(1-phenylethyl)ammonium hydroxide or 1-phenylethylamine, followed by conventional separation of the diastereoisomeric mixture of salts thus obtained, for example by fractional crystallisation from a suitable solvent, for example a (1-4C)alkanol, whereafter the optically active form of said compound of formula I may be liberated by treatment with acid using a conventional procedure for example using an aqueous mineral acid such as dilute hydrochloric acid. Similarly, when an optically active form of a compound of formula I wherein Rc is other than hydroxy is required, it may be obtained using the aforementioned esterification or sulphonamidation procedures using the appropriate optically active form of said acid.

Further it will be appreciated that when a compound of formula I wherein Ra or Rb is hydroxyphenyl, or benzene ring B bears a hydroxy substituent is required, this may conveniently be obtained by carrying out reaction (i) and (ii) hereinabove using a corresponding furan of formula II and diol of formula III in which the aromatic hydroxy substituent is protected, for example as a trimethylsilyl, (1-6C)alkyl (such as methyl or ethyl) or acyl (such as acetyl or benzoyl) derivative, followed by an extra and final deprotection step. A process incorporating such a deprotection step after reactions (i) and (ii) is also provided as a feature of the invention.

The deprotection conditions required necessarily depend on the protecting groups concerned. Thus, for example, when it is methyl or ethyl the deprotection may be carried out, for example, by heating with sodium thioethoxide in a suitable solvent (such as N,N-dimethylformamide) at an elevated temperature, for example 90°-160° C. Similarly, when the protecting group is acyl, it may be removed, for example by hydrolysis in the presence of a base (such as sodium or potassium hydroxide) in a suitable aqueous solvent [such as a (1-4C)alkanol or a glycol] at a temperature in the range, for example, 10°-60° C. Similarly in the case of a trimethylsilyl protecting group, it may be removed for example, by reaction with aqueous tetrabutylammonium fluoride or sodium fluoride in conventional manner.

The Wittig reaction involved in step (i) in general produces compounds of formula I in which the carbon atoms adjacent to the vinylene group have predominantly cis-relative stereochemistry i.e. the "Z" isomer. However, the compounds of formula I having trans-relative stereochemistry (i.e. the "E" isomer) are also formed in the process and may be obtained by conventional separation of the mixture of "Z"- and "E"-isomers first obtained.

The reaction step (i) is conveniently performed in a suitable solvent or diluent, for example an aromatic solvent such as benzene, toluene or chlorobenzene, and ether such as 1,2-dimethoxyethane, dibutyl ether, tetrahydrofuran, dimethyl sulphoxide or tetramethylene sulphone, or in a mixture of one or more such solvents or diluents. Reaction step (i) is generally performed at a temperature in the range, for example, −80° C. to 40° C. but is conveniently performed at or near room temperature, that is in the range 15° to 35° C. Reaction step (i) may be operated quite independently of step (ii), since the erythro-diols of formula III are useful chemical intermediates for the production of other compounds besides those of formula I.

The ylid starting materials may be obtained by procedures analogous to those well known in the art. Thus, they may be obtained by treating a phosphonium halide of the formula:

$$(Rd_3)P^+.CH_2.Y.COQa \quad Z^-$$

wherein Rd and Y have the meanings stated above and Qa is hydroxy or (1–6C)alkanesulphonamido and Z is halide, with a strong base such as sodium hydride, lithium diisopropylamide, potassium t-butoxide or butyllithium in a suitable solvent such as that used for the Wittig reaction itself. The ylid starting materials are generaly formed in situ immediately prior to carrying out the process of the invention.

Aldehydes of formula II having the required erythro-diol configuration may be conveniently formed in solution as the corresponding alkali metal salts by reaction of a [2,3-trans]-tetrahydro-5-hydroxy-3-hydroxymethyl-2-phenylfuran of the formula IIa (that is the corresponding lactol formed from the aldehyde of formula II) with an alkali metal derived base, such as potassium t-butoxide or butyllithium, in a suitable inert solvent, and this is the basis for the invention. The aldehydes of formula II are preferably generated and reacted as required in situ. The invention thus also provides a process for the production of a diol of the formula III which comprises carrying out step (i) of the above process but using a lactol of formula IIa as original starting material to generate the aldehyde II in situ.

In the cyclisation reaction (ii), a suitable (1–6C)alkanesulphonyl ester is, for example, a methanesulphonyl or ethanesulphonyl mono-ester and a suitable arenesulphonyl ester is, for example, a benzenesulphonyl or p-toluenesulphonyl mono-ester.

The carbonyl compound of the formula RaRb.CO (or its hydrate, or its acetal or hemiacetal with a (1–4C)alkanol) is preferably used in excess.

When the free diol of formula III is used the reaction (ii) is carried out in the presence of an acid catalyst, for example, hydrogen chloride, hydrogen bromide, sulphuric acid, phosphoric acid, p-toluenesulphonic acid or the anionic form of a sulphonated polystyrene catalyst, conveniently in a suitable solvent or diluent, for example an ether such as diethyl ether, dibutyl ether, 1,2-dimethoxyethane or tetrahydrofuran, and at a temperature in the range, for example, 10° to 120° C. In some cases sufficient acid catalyst may be provided by the inherent acidity of the starting diol of formula III wherein Rc is hydroxy.

When a monosulphonyl ester of a diol of formula III is used, the cyclisation reaction (ii) is carried out first in the presence of an acid catalyst, for example under the conditions described above to produce an intermediate of the formula IIIa, wherein one of Xa and Xb is alkanesulphonyl or arenesulphonyl, and the other is a group of the formula —CRaRb.OH. The latter intermediate may then be cyclised in situ to the required compound of the formula I by addition of a suitable base, for example, sodium hydride, butyllithium or potassium carbonate, in a suitable solvent or diluent, for example in the ether solvent used for the acid catalysed step above, and at a temperature in the range, for example, 30°–100° C.

The mono-sulphonyl esters may be made by any conventional procedures, for example by reacting one molecular equivalent of the apropriate alkanesulphonyl or arenesulphonyl halide, for example methanesulphonyl chloride or p-toluenesulphonyl chloride, in a suitable solvent or diluent (such as an ether or dichloromethane) and in the presence of a base such as pyridine or triethylamine.

The majority of erythro-diols of formula III are disclosed in general in EPA No. 94239. The aldehydes of formula II and the corresponding [2,3-trans]-tetrahydro-5-hydroxy-3-hydroxymethyl-2-phenylfurans of formula IIa, wherein Q, Y and benzene ring B have the meanings set out hereinbefore, are novel and are provided as further features of the invention.

The invention also provides a process for the manufacture of a [2,3-trans]-tetrahydrofuran derivative of formula II which comprises selectively reducing a [2,3-trans]-lactone of the formula IV wherein benzene ring B has the meaning set out hereinbefore.

The selective reduction may be carried out using any suitable reducing agent known to selectively reduce the lactone carbonyl group to the corresponding lactol. Thus, typical reducing agents are, for example, diisobutylaluminium hydride or sodium (t-butoxy)bis(2-methoxyethoxy)aluminium hydride The reduction is preferably performed in a suitable solvent or diluent, for example an ether such as diethyl ether, 1,2-dimethoxyethane or tetrahydrofuran, conveniently diluted with a hydrocarbon solvent such as benzene, toluene or xylene, and at a temperature in the range, for example, −80° to +20° C.

The lactones of formula IV may themselves be obtained by selective reduction of a trans-phenylparaconic acid of the formula V (or a derivative thereof), which reductive process is provided as a further feature of the invention.

This selective reduction may be carried out by means of any suitable reducing agent known to selectively reduce carboxylic acid groups in the presence of lactone carbonyl groups. Thus, for example typical reducing agents are diborane or alkali metal borohydrides (such as sodium borohydride) in the presence of a Lewis acid such as tin(IV) chloride. Examples of suitable derivatives are, for example acid halides such as acid chlorides or bromides. The reduction is preferably carried out in a suitable solvent or diluent, for example as mentioned hereinabove for the preparation the compounds of formula II, and at a temperature in the range, for example, 0° to 35° C.

The lactones of formula IV and certain of the paraconic acids of formula V wherein benzene ring B has the meanings set out herein are novel and are provided as still further features of the invention.

The paraconic acids of formula V may be made by the base-catalysed reaction of a suitable benzaldehyde of the formula VI with succinic anhydride and this process addressed to novel acids of formula V is provided as a further feature of the invention.

A suitable base catalyst is, for example sodium acetate or zinc chloride triethylamine complex. However other base catalysts previously used for the production of known paraconic acids (such as phenylparaconic acid) may also be employed. A suitable solvent or diluent, for example methylene chloride may be used. The reaction may also be performed in the absence of solvent. A convenient temperature is, for example in the range, 10° C. to 130° C.

The procedure may give rise to both cis-paraconic acids of formula Va as well as the required trans-paraconic depending on the reaction conditions. However the acids of formula Va may be readily converted to the thermodynamically more stable trans-isomer of formula V by treatment with strong acid. The latter process is also provided as a feature of the invention. A suitable strong acid is, for example a mineral acid such as sulphuric or phosphoric acid, or an organic acid such as p-toluenesulphonic or trifluoroacetic acid.

It will be appreciated that when a compound of formula I which is in optically active form is required, it is possible to produce such a compound by starting with a single, optically active, enantiomeric form of a trans-paraconic acid of formula V and carrying out the aforementioned processes via the intermediates of formula IV, IIa, II and III. Such a combined process, whether for the production of a racemic or a single optically active form of a compound of formula I as defined hereinabove but wherein n is 1, A is vinylene and Rc is hydroxy or (1-6C)alkanesulphonamido, is provided as a further feature of the invention.

The invention, accordingly, also provides the novel intermediates of formula V, IV, and IIa and II as defined hereinbefore in separate optically active forms as well as in racemic form.

It will be understood that one or more of the above procedures may be carried out in succession in the same reaction vessel and without the isolation or purification of the appropriate intermediate.

The invention will now be illustrated by the following non-limiting Examples in which, unless otherwise stated:

(i) evaporations were carried out on a rotary evaporator in vacuo;

(ii) operations were carried out at room temperature, that is in the range 18° to 26° C.;

(iii) the progress of chemical reactions was assessed by thin layer chromatography (TLC) on 0.25 mm. Kieselgel 60F 254 plates (Art. 5715), available from E Merck, Darmstadt, W. Germany.

(iv) NMR spectra were determined at 90 MHz in $CDCl_3$ using tetramethylsilane (TMS) as an internal standard and expressed as chemical shifts (delta values) in parts per million relative to TMS for major peaks, using the following abbreviations for designation of peaks: s, singlet; d, doublet; t, triplet; m, multiplet; br, broad;

(v) yields are provided for illustration and do not represent the maximum attainable by diligent development of the disclosed procedures; and (vi) end-products were characterised by standard techniques of micro-analysis, infra-red, NMR and/or mass spectral analysis.

EXAMPLE 1

This Example illustrates the production of a paraconic acid of formula V.

Succinic anhydride (22 g.), o-methoxybenzaldehyde (20 g.) and anhydrous zinc chloride (44 g.) were added to dichloromethane (dried over alumina, 200 ml.) and the mixture stirred under argon. Triethylamine (41 ml.) was added to the ice-cooled mixture over a period of 20 minutes. The reaction mixture was then stirred at 20°-25° C. for 18 hours, after which time hydrochloric acid (2M, 130 ml.) and ethyl acetate (200 ml.) were added. The subsequent mixture was stirred for 5 minutes. The aqueous phase was separated and extracted with ethyl acetate (150 ml.) The combined extracts were washed with saturated brine (50 ml.) and then extracted with saturated sodium bicarbonate solution (3×200 ml.). The combined aqueous extracts were washed with ethyl acetate, and then acidified to pH 2 with concentrated hydrochloric acid. The oil which separated was extracted into ethyl acetate (2×150 ml.). The combined extracts were washed with saturated brine (4×50 ml.) until acid free, then dried ($MgSO_4$) and evaporated. Toluene (300 ml.) was added to the residue and the mixture was distilled atmospheric pressure until the residual material attained 110° C. On cooling to 20° C., tetrahydro-2-o-methoxyphenyl-5-oxo-3-furancarboxylic acid separated as a crystalline white solid (27.2 g., 78%) (m.p. 106° C.) which was shown by NMR to be a mixture of [2,3-cis-]- and [2,3-trans]-isomer: 2.8–3.0 (2H, m), 3.1–3.6 (1H, m), 3.8 (3H, s), 5.82 (¾H, d) [trans], 5.95 (¼H, d) [cis], 6.8–7.5 (4H, m).

EXAMPLE 2

This Example illustrates the isomerisation of a cis- to a trans-paraconic acid of formula V.

A mixture of [2,3-cis]- and [2,3-trans]-tetrahydro-2-o-methoxyphenyl-5-oxo-3-furancarboxylic acid (188.6 g.) was added to an ice cooled solution of concentrated sulphuric acid (320 ml.) in water (480 ml.) and stirred at 20°-25° C. for 18 hours. Water (800 ml.) was then added and the mixture extracted with ethyl acetate (2×750 ml.). The combined extracts were washed with brine (4×500 ml.) until acid free, dried ($MgSO_4$) and evaporated to low volume. Toluene (1 liter) was added and the distillation continued at atmospheric pressure until the residual material attained a temperature of 110° C. On cooling pure [2,3-trans]-tetrahydro-2-o-methoxyphenyl-5-oxo-3-furancarboxylic acid separated as a white crystalline solid (169.5 g., 90%), m.p. 133°-134° C.; NMR: 2.8–3.0 (2H, d), 3.3–3.6 (1H, m), 3.8 (3H, s), 5.82 (1H, d), 6.8–7.4 (4H, m).

EXAMPLE 3

This Example illustrates the selective reduction of a paraconic acid of formula V to give a lactone of formula IV.

Borane solution in tetrahydrofuran(THF) (1M, 254 ml.) was added during 15 minutes to a stirred solution of [2,3-trans]-tetrahydro-2-o-methoxyphenyl-5-oxo-3-furancarboxylic acid (20 g.) in THF (50 ml.) at 20° to 25° C. After a further 45 minutes water (10 ml.) was added slowly to destroy excess borane, followed by saturated potassium carbonate solution (50 ml.). The mixture was well agitated and allowed to separate. The aqueous phase was extracted with ethyl acetate (250 ml.). The organic phases were combined, washed with saturated brine (50 ml.), dried ($MgSO_4$) and evaporated to dryness to yield [4,5-trans]-tetrahydro-4-hydroxymethyl-5-o-methoxyphenylfuran-2-one (18.0 g.) as a viscous, colourless oil, essentially pure by TLC and NMR spectroscopic analysis.

EXAMPLE 4

This Example illustrates the selective reduction of a lactone of formula IV to a lactol of formula IIa.

Diisobutylaluminium hydride solution in toluene (1.23M, 35.3 ml.) was added during 15 minutes to a stirred solution of [4,5-trans]-tetrahydro-4-hydroxymethyl-5-o-methoxyphenylfuran-2-one (4.5 g.) in toluene (20 ml.) and 1,2-dimethoxyethane (4 ml.) cooled at −60° to −70° C.* under argon. After 20 minutes, methanol (6 ml.) was added and the reaction mixture was allowed to attain room temperature. Saturated brine (50 ml.) and ethyl acetate (100 ml.) were then added and the mixture was stirred vigorously for 15 minutes. Insoluble material was removed by filtration through diatomaceous earth. The phases were separated and the aqueous phase extracted with ethyl acetate (50 ml.). The combined organic phases were dried (MgSO4), evaporated and the residue recrystallised from toluene to give [2,3-trans]-tetrahydro-5-hydroxy-3-hydroxymethyl-2-o-methoxyphenylfuran (4.18 g.) as a white, crystalline solid, m.p. 110°–111° C. (mixture of C5 epimers) of satisfactory purity, as judged by NMR spectroscopy, for further use. [* The above reduction may also be carried out satisfactorily, but with reduced yield, at a temperature of 0° to 5° C.]

EXAMPLE 5

This Example illustrates the formation of an erythrodiol of formula III.

A mixture of (4-carboxybutyl)triphenylphosphonium bromide (61.4 g.) and potassium t-butoxide (31.0 g.) in dry toluene (500 ml.) was heated to 90° C. for 30 minutes to form the cherry red ylid solution. A portion (210 ml) of this solution was then added to a solution of [2,3-trans]-tetrahydro-5-hydroxy-3-hydroxymethyl-2-o-methoxyphenylfuran (4.18 g.) in dry tetrahydrofuran (50 ml.) under argon. The reaction produces the dipotassium salt of erythro-4-hydroxy-3-hydroxymethyl-4-o-methoxyphenylbutyraldehyde in situ which reacts with the ylid. TLC analysis indicated the reaction was complete after 10 minutes. Water (220 ml.) was then added with vigorous stirring. The phases were separated and the aqueous phase extracted with ether (4×100 ml.).

The extracts and solid interphase were discarded. The aqueous phase was acidified to pH 4 with saturated oxalic acid solution and extracted with ethyl acetate (3×200 ml.). These combined extracts were evaporated to dryness. The white solid obtained was washed with ethyl acetate and the solid discarded. The washings were then extracted with saturated sodium bicarbonate solution (3×250 ml.). The aqueous extracts were again acidified to pH 5 with saturated oxalic acid solution and the precipitated material extracted with ethyl acetate (2×250 ml.). [In all extractions solid interphase material was removed by filtration]. The ethyl acetate extracts were evaporated and the residue dried by azeotropic distillation with toluene. There was thus obtained erythro-5-(Z)-9-hydroxy-8-hydroxymethyl-9-o-methoxyphenyl-5-nonenoic acid as a colourless oil (2.8 g.); NMR (400 MHz): 1.50 (6H, m), 2.22 (9H, m), 3.9 (3H, s), 4.0 (2H, m), 5.3 (3H, m), 7.1 (4H, m), 9.5 (1H, br s).

EXAMPLE 6

Using analogous procedures to those described in Examples 3–5, but starting from the known compound [2,3-trans]-tetrahydro-5-oxo-2-phenyl-3-furancarboxylic acid, there may be obtained 5(Z)-erythro-9-hydroxy-8-hydroxymethyl-9-phenylnonenoic acid as a viscous oil; NMR (400 MHz): 1.4–2.2 (7H, m), 2.86 (2H, t, J=7 Hz), 3.68 (2H, d), 4.8 (3H, br s), 4.99 (1H, d J=3.6 Hz), 5.2–5.6 (2H, m), 7.33 (5H, s). The following intermediates may be isolated:

(i) [4,5-trans]-tetrahydro-4-hydroxymethyl-5-phenylfuran-2-one; and (ii) [2,3-trans]-tetrahydro-5-hydroxy-3-hydroxymethyl-2-phenylfuran (mixture of C5 epimers).

EXAMPLE 7

This Example illustrates the cyclisation of an erythrodiol of formula III to give a dioxane of formula I.

A solution of erythro-5(Z)-9-hydroxy-8-hydroxymethyl-9-o-methoxyphenyl 5-nonenoic acid (2.8 g.) is 2,2-dimethoxypropane (10 ml.) was treated with p-toluenesulphonic acid (0.05 g.). After 1 hour ether (10 ml.) and triethylamine (0.1 ml.) were added. The solvents were evaporated and the residue was dissolved in ether (20 ml.). The solution was washed with water (3×10 ml.), then with saturated brine (10 ml.), dried (MgSO4) and evaporated. The oily residue was extracted with boiling petrol (60°–80° C.) and the solution allowed to cool. There was thus obtained 5(Z)-7-(2,2-dimethyl-4-o-methoxyphenyl-1,3-dioxan-cis-5-yl)heptenoic acid as a white crystalline solid (0.7 g.), m.p. 112°–114° C., having a satisfactory NMR spectrum: 1.55 (6H, d), 2.25 (2H, t), 1.1–2.7 (7H, m), 3.6–4.3 (2H, m), 3.85 (3H, s), 5.1–5.6 (3H, m), 6.80–8.0 (4H, m), 10.3 (1H, br).

Using a similar procedure to that described in Example 7 but starting from 5(Z)-erythro-9-hydroxy-8-hydroxymethyl-9-phenylnonenoic acid, 5(Z)-7-(2,2-dimethyl-4-phenyl-1,3-dioxan-cis-5-yl)-heptenoic acid may be obtained as a solid, m.p. 86°–86.5° C. (after 3 recrystallisations from hexane).

EXAMPLE 9

Using similar procedures to those described in Examples 3, 4, 5 and 7, the following compounds of formula Ib may be obtained by the processes of the invention via the corresponding intermediate diols of formula III, aldehydes of formula II, lactols of formula IIa, lactones of formula IV and carboxylic acids of formula V:

| No. | Ra | Rb | Benzene Ring B |
| --- | --- | --- | --- |
| 1 | methyl | methyl | 3-fluorophenyl |
| 2 | methyl | methyl | 3-chlorophenyl |
| 3 | methyl | methyl | 2-methylphenyl |
| 4 | methyl | H | phenyl |
| 5 | isopropyl | H | phenyl |
| 6 | ethyl | ethyl | phenyl |
| 7 | ethyl | ethyl | 2-fluorophenyl |
| 8 | 2-chlorophenyl | H | phenyl |
| 9 | 2-methylphenyl | H | phenyl |
| 10 | 2-ethylphenyl | H | phenyl |
| 11 | 3-fluorophenyl | H | phenyl |
| 12 | 3-chlorophenyl | H | phenyl |
| 13 | 3-methylthiophenyl | H | phenyl |
| 14 | 4-fluorophenyl | H | phenyl |
| 15 | 4-chlorophenyl | H | phenyl |
| 16 | 4-methoxyphenyl | H | phenyl |
| 17 | 3,4-methylene dioxyphenyl | H | phenyl |
| 18 | 3,4-(methylene- | H | phenyl |

| No. | Ra | Rb | Benzene Ring B |
|---|---|---|---|
| 19 | oxymethylene)-pentamethylene* | | phenyl |
| 20 | hexamethylene* | | phenyl |
| 21 | (3-methyl)pentamethylene* | | |

*Note: Ra + Rb taken together.

EXAMPLE 10

The following additional sulphonamidation procedure illustrates the production of compounds of formula I wherein Rc is (1-6C)alkanesulphonamido:

A solution containing 5(Z)-7-(2,2-dimethyl-4-phenyl-1,3-dioxan-cis-5-yl)heptenoic acid (318 mg.), 4-dimethylaminopyridine (122 mg.) and methanesulphonamide (95 mg.) in dry dichloromethane (20 ml.) was treated with a solution of dicyclohexylcarbodiimide (206 mg.) in dichloromethane (2 ml.). The mixture was stirred overnight, filtered, and the filtrate was evaporated. The residual oil was partitioned between saturated aqueous sodium cabonate solution (50 ml.) and ether (50 ml.), and the aqueous phase was washed with more ether (2×25 ml.). The aqueous phase was acidified with hydrochloric acid (2M) and extracted with ethyl acetate (3×25 ml.). The combined extracts were washed with saturated brine, dried (MgSO4) and evaporated to give an oil which on column chromatography, eluting with toluene/ethyl acetate/acetic acid (80:20:2 v/v) gave N-methanesulphonyl-5(Z)-7-(2,2-dimethyl-4-phenyl-1,3-dioxan-cis-5-yl)heptenamide, as a colourless oil (100 mg.); NMR: 1,2–2.5 (9H, m), 1.55 (6H, s), 3.25 (3H, s), 3.7–4.3 (2H, m), 5.1–5.5 (3H, m), 7.1–7.4 (5H, br.s), 8.4 (1H, br s).

EXAMPLE 11

The following additional deprotection procedure illustrates the production of compounds of the formula I wherein one of Ra, Rb and benzene ring B bears an aromatic hydroxy group:

A portion (2.1 ml.) of a 0.5M solution of sodium thioethoxide in N,N-dimethylformamide was added under nitrogen to 5(Z)-7-(2,2-dimethyl-4-o-methoxyphenyl-1,3-dioxan-cis-5-yl)heptenoic acid (104 mg.). The mixture was heated under reflux for 1.1 hours and then diluted with ice-water to a total volume of 25 ml. The aqueous mixture was acidified to pH 4 with acetic acid and extracted with ethyl acetate (2×15 ml.). The extracts were washed with saturated brine, dried (MgSO4) and evaporated. The oil obtained was purified by column chromatography on silica (12 g.) eluting with 80:20:2 (by volume) toluene/ethyl acetate/acetic acid to give 5(Z)-7-(2,2-dimethyl-4-o-hydroxyphenyl-1,3-dioxan-cis-5-yl)heptenoic acid as an oil (25 mg.); NMR (400 MHz): 1.50 (6H, s), 2.22 (9H, m), 3.97 (2H, m), 5.31 (3H, m), 6.98 (4H, m), 8.38 (2H, s).

EXAMPLE 12

This Example demonstrates isomerisation of a cis- to a trans-paraconic acid of formula V.

A mixture of [2,3-cis]- and [2,3-trans]-tetrahydro-2-o-methoxyphenyl-5-oxo-3-furancarboxylic acid (1.0 g.) and p-toluenesulphonic acid monohydrate (0.15 g.) in toluene (20 ml.) was heated under reflux for 2 hours. The hot solution was then allowed to cool to give a white crystalline precipitate enriched in [2,3-trans]-tetrahydro-2-o-methoxyphenyl-5-oxo-3-furancarboxylic acid, as judged by NMR spectroscopy.

EXAMPLE 13

This Example illustrates the production of an optically active form of a compound of formula I:

(i) A solution of d-ephedrine (61.2 g.) in hot ethyl acetate (150 ml.) was added to a solution of [2,3-trans]-tetrahydro-2-o-methoxyphenyl-5-oxo-3-furancarboxylic acid (87.6 g.) in hot ethyl acetate (350 ml.). The mixture was allowed to cool to room temperature during 2 hours and the crystalline salt which had formed was separated by filtration to give 62 g. of solid material having $^{25}[\alpha]_D + 40.2°$ (methanol). This material was recrystallised twice from ethyl acetate to give 48 g. of optically pure solid $^{25}[\alpha]_D + 50.3°$ (methanol). This solid was added to ethyl acetate (1 liter) and 2M hydrochloric acid (150 ml.). The ethyl acetate layer was washed with brine (2×100 ml.) until the pH of the washings was pH 2-3, and then dried (MgSO4) and evaporated. The residue was dissolved in boiling toluene (200 ml.). Insoluble material was removed by hot filtration. The filtrate was allowed to cool to give (+)-[2,3-trans]-tetrahydro-2-o-methoxyphenyl-5-oxo-3-furancarboxylic acid (A) (27.4 g.) $^{25}[\alpha]_D + 33.0°$ (methanol). Recrystallisation from toluene gave material of $^{25}[\alpha]_D + 33.8°$ (methanol), m.p. 125°–127° C. (decomposition), shown to be >98% optically pure by conversion of a small sample to its (−)-amyl ester and examination of the $^{13}C$ NMR spectrum.

(ii) A solution of A (97.5 g.) in dry tetrahydrofuran (150 ml.) was cooled to 15° C. and treated with a solution of borane in tetrahydrofuran (500 ml. of a 1M solution) with the temperature maintained at 20°–25° C. After 30 minutes the reaction was complete (as judged by TLC analysis) and water (200 ml.) was added slowly to decompose the excess borane. The mixture was concentrated in vacuo and the residue was mixed with ethyl acetate (500 ml.). The organic layer was washed successively with saturated potassium carbonate solution (2×100 ml.) and saturated brine, dried (MgSO4), and evaporated to give [4,5-trans]-tetrahydro-4-hydroxymethyl-5-o-methoxyphenylfuran-2-one (B) as a viscous oil (81.8 g.), having $^{25}[\alpha]_D - 14.2°$ (methanol) and a satisfactory NMR spectrum (d6-acetone): 2.6 (3H, m), 3.7 (2H, m), 3.8 (3H, s), 4.1 (1H, br), 5.55 (1H, m), 6.8–7.5 (4H, m).

(iii) A solution of B (obtained above) in 1,2-dimethoxyethane (150 ml.) and dry toluene (500 ml.) was cooled under a nitrogen atmosphere to −60° C. A toluene solution of diisobutylaluminium hydride (672 ml. of 1.23M solution) was then added slowly. After 30 minutes the reaction was quenched by addition of methanol (50 ml.) and the mixture allowed to warm up to room temperature. 2M Hydrochloric acid (1 liter) and ethyl acetate (500 ml.) were then added and the mixture stirred. The aqueous phase was separated and extracted with ethyl acetate (2×500 ml.). The ethyl acetate phase and extracts were combined, dried (MgSO4) and evaporated. The residual oil was dissolved in hot toluene (500 ml.). The solution obtained gave on cooling (−)-[2,3-trans]-tetrahydro-5-hydroxy-3-hydroxymethyl-2-o-methoxyfuran (C) as a white solid (63.3 g.), $^{25}[\alpha]_D - 24.2°$ (methanol, m.p. 110°–111° C., having a satisfactory NMR spectrum: 1.5–2.4 (3H, m), 3.4–4.0 (2H, m), 3.8 (3H, s) 4.2–4.8 (2H, br), 5.25 (1H, m), 5.6 (1H, m), 6.8–7.9 (4H, m).

(iv) A solution of C (63.3 g.) in dry tetrahydrofuran (200 ml.) was added at ambient temperature to a red ylid solution [obtained by heating 4-carboxybutyl)phosphonium bromide (505 g.) and potassium t-butoxide (255.5 g.) in dry toluene (2 liters) at 90° C. under a nitrogen atmosphere]. The red mixture obtained [which contained the dipotassium salt of (−)-erythro-4-hydroxy-3-hydroxymethyl-4-o-methoxyphenyl-butyraldehyde in situ] was stirred for 20 minutes after which time TLC analysis indicated complete reaction. Water (1 liter) was then added. The phases were separated and the aqueous phase extracted with ethyl acetate (3×500 ml.). The extracts were discarded. The aqueous phase was then acidified (pH 4) by addition of oxalic acid and then extracted with ethyl acetate. The combined extracts were washed with saturated brine, dried (MgSO$_4$) and evaporated. The residue was triturated with ethyl acetate (100 ml.) and solid material removed by filtration. The filtrate was evaporated to give (−)-erythro-5(Z)-9-hydroxy-8-hydroxymethyl-9-o-methoxyphenyl-5-nonenoic acid (D) as a viscous oil (65.9 g.) $^{25}[\alpha]_D$−61° (methanol), having an NMR spectrum essentially the same as that in Example 5.

(v) A mixture of D(2.0 g.) and p-toluenesulphonic acid (50 mg.) in 2,2-dimethoxypropane (10 ml.) was stirred for 1 hour. Triethylamine (1 ml.) and ether (10 ml.) were then added and the mixture evaporated. The residue was extracted with ether (30 ml.). The ethereal solution was washed with water (2×10 ml.), dried (MgSO$_4$) and evaporated. The residual oil was purified by chromatography on silica (30 g.) using 25% v/v ethyl acetate in toluene as eluant to give (−)-5-(Z)-7-(2,2-dimethyl-4-o-methoxyphenyl-1,3-dioxan-cis-5-yl)heptenoic acid as a viscous oil (1.5 g.), $^{25}[\alpha]_D$−127.6° (ethyl acetate), having an NMR spectrum essentially identical with that given in Example 7.

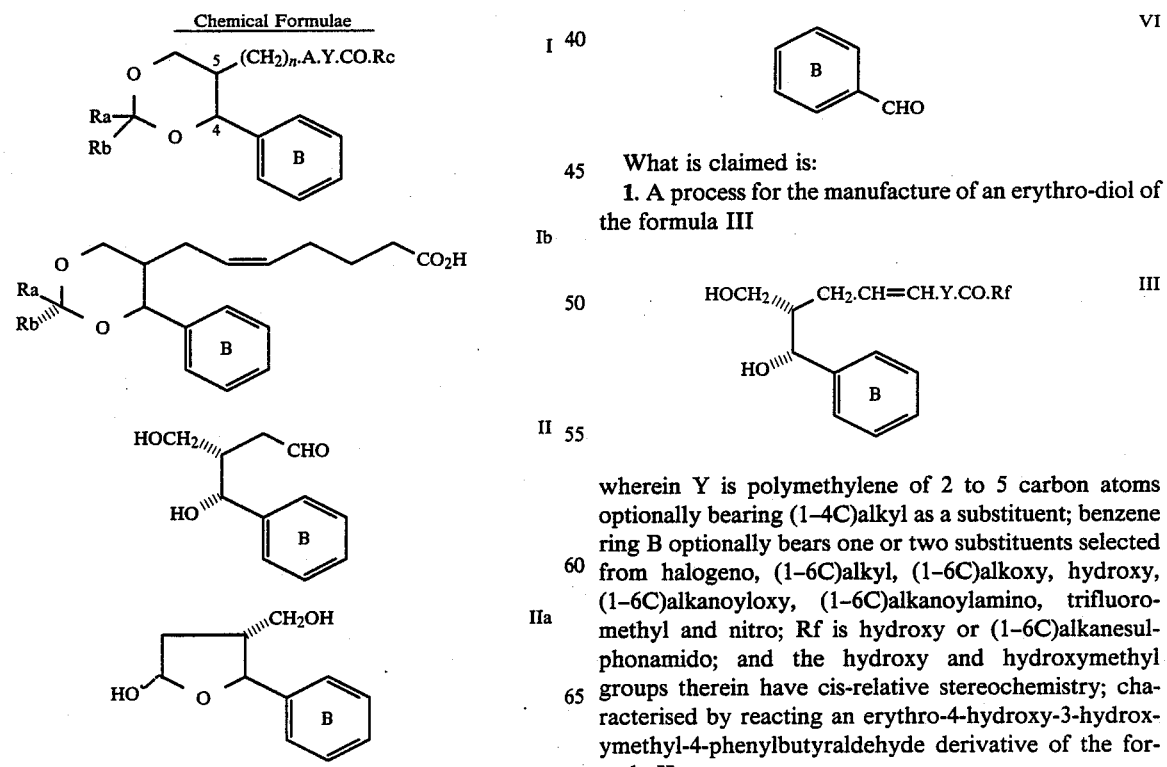

What is claimed is:

1. A process for the manufacture of an erythro-diol of the formula III wherein Y is polymethylene of 2 to 5 carbon atoms optionally bearing (1–4C)alkyl as a substituent; benzene ring B optionally bears one or two substituents selected from halogeno, (1–6C)alkyl, (1–6C)alkoxy, hydroxy, (1–6C)alkanoyloxy, (1–6C)alkanoylamino, trifluoromethyl and nitro; Rf is hydroxy or (1–6C)alkanesulphonamido; and the hydroxy and hydroxymethyl groups therein have cis-relative stereochemistry; characterised by reacting an erythro-4-hydroxy-3-hydroxymethyl-4-phenylbutyraldehyde derivative of the formula II,

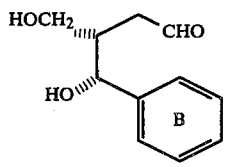

wherein benzene ring B has the above meaning and the hydroxy and hydroxymethyl groups therein have cis-relative stereochemistry, or an alkali metal salt thereof; with an ylid of the formula $(Rd)_3P=CH.Y.CO.Q$, wherein Rd is (1–6C)alkyl or aryl, Q stands for —OM or —NM.$SO_2$Re in which M is an alkali metal and Re is (1–6C)alkyl, and Y has the above defined meaning, followed by acidification of the reaction mixture.

2. A process according to claim 1 characterised in that the butyraldehyde derivative of formula II is generated in situ from the corresponding [2,3-trans]-tetrahydro-3-hydroxymethyl-5-hydroxy-2-phenylfuran of the formula IIa

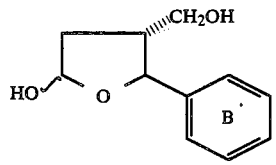

wherein benzene ring B has the meanings defined in claim 1.

* * * * *